United States Patent
Cheng et al.

(10) Patent No.: US 9,459,224 B1
(45) Date of Patent: Oct. 4, 2016

(54) GAS SENSOR, INTEGRATED CIRCUIT DEVICE USING THE SAME, AND MANUFACTURING METHOD THEREOF

(71) Applicant: TAIWAN SEMICONDUCTOR MANUFACTURING CO., LTD., Hsinchu (TW)

(72) Inventors: Chun-Wen Cheng, Zhubei (TW); Chia-Hua Chu, Zhubei (TW); Fei-Lung Lai, New Taipei (TW); Shiang-Chi Lin, Taoyuan (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 0 days.

(21) Appl. No.: 14/788,352

(22) Filed: Jun. 30, 2015

(51) Int. Cl.
*H01L 27/14* (2006.01)
*G01N 27/16* (2006.01)
*H01L 49/02* (2006.01)
*H01L 21/768* (2006.01)
*H01L 23/31* (2006.01)

(52) U.S. Cl.
CPC ......... *G01N 27/16* (2013.01); *H01L 21/76802* (2013.01); *H01L 23/3121* (2013.01); *H01L 28/60* (2013.01)

(58) Field of Classification Search
CPC .............. H01L 21/76802; H01L 23/3121; H01L 28/60; G01N 27/16
USPC ................................................. 257/414, 467
See application file for complete search history.

(56) References Cited

U.S. PATENT DOCUMENTS

| | | | | |
|---|---|---|---|---|
| 2002/0142478 A1* | 10/2002 | Wado | ................... | G01N 27/124 436/151 |
| 2009/0129440 A1* | 5/2009 | Opitz | ........................ | G01J 5/10 374/178 |
| 2010/0147052 A1* | 6/2010 | Nelson | ............... | G01N 15/0656 73/28.01 |
| 2012/0266646 A1* | 10/2012 | Maeda | ................ | F02D 41/1466 73/1.06 |
| 2014/0069185 A1* | 3/2014 | Tu | ........................... | G01F 1/688 73/204.26 |
| 2014/0113828 A1* | 4/2014 | Gilbert | .................. | H01L 39/126 505/100 |
| 2016/0009546 A1* | 1/2016 | Zhang | ................... | B81B 7/0019 257/419 |

FOREIGN PATENT DOCUMENTS

JP 2014-228447 A * 8/2014 ............. G01N 27/12

* cited by examiner

*Primary Examiner* — Long K Tran
(74) *Attorney, Agent, or Firm* — Maschoff Brennan

(57) ABSTRACT

A gas sensor includes a substrate, a heater, a dielectric layer, a sensing electrode, and a gas sensitive film. The substrate has a sensing region and a peripheral region surrounding the sensing region, and the substrate further has an opening disposed in the sensing region. The heater is disposed at least above the opening, and the heater has an electrical resistivity larger than about $6 \times 10^{-8}$ ohm-m. The dielectric layer is disposed on the heater. The sensing electrode is disposed on the dielectric layer. The gas sensitive film is disposed on the sensing electrode.

17 Claims, 11 Drawing Sheets

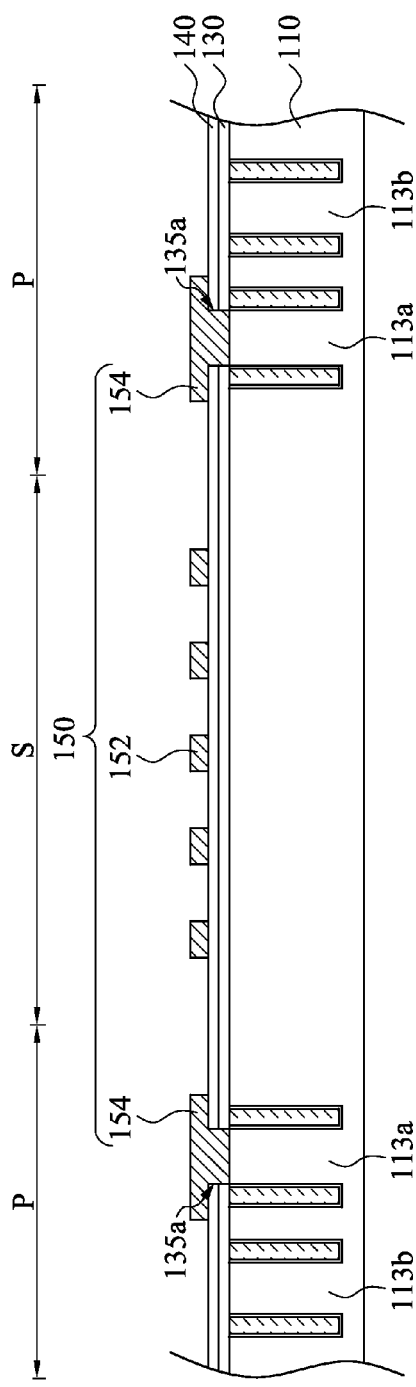
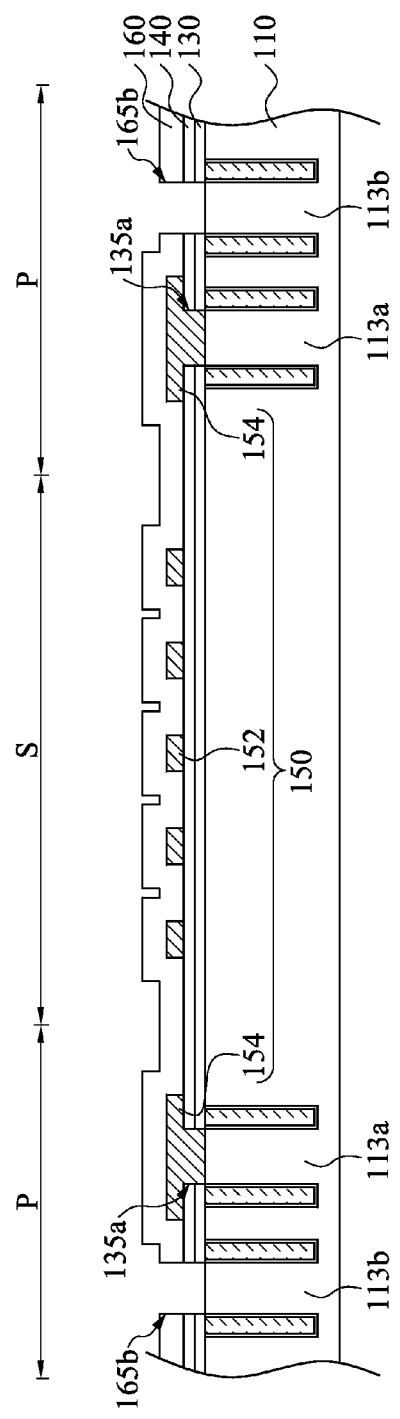
Fig. 1C
Fig. 1D

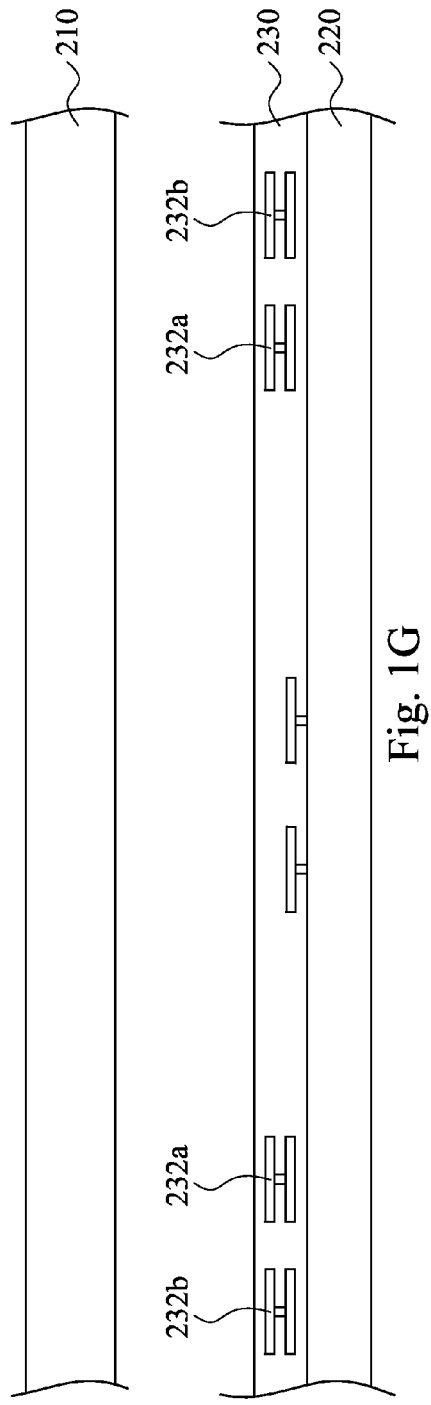
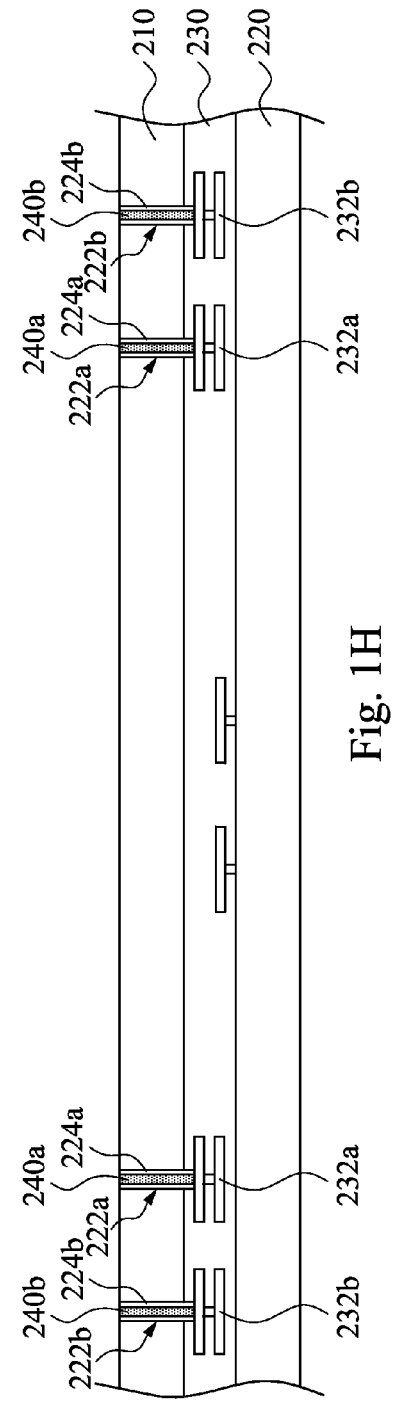

GAS SENSOR, INTEGRATED CIRCUIT DEVICE USING THE SAME, AND MANUFACTURING METHOD THEREOF

BACKGROUND

MEMS (Micro Electro Mechanical System) technologies have become quite prevalent in the semiconductor manufacturing industry. A MEMS device is a piece of technology with components on a very small scale. MEMS devices are micro-sized devices or machines that may have stationary and/or movable elements that provide some type of electromechanical functionality desired for a particular application and system. Some MEMS devices which may be found in a semiconductor chip package include, for example without limitation, micro-timing devices, micro-sensors, micro-actuators, accelerometers, micro-switches, micro-pumps and valves, and others that support and assist with controlling the functionality of the chip(s) in the package and/or system-level IC. Such MEMS devices offer numerous advantages over traditional sensors, as they are typically more cost efficient, reliable, relatively easy to manufacture, and there is often very good repeatability between devices.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIGS. 1A-1L are cross-sectional view of the method of forming an integrated circuit device in accordance with various embodiments of the present disclosure.

DETAILED DESCRIPTION

Figure 1A:
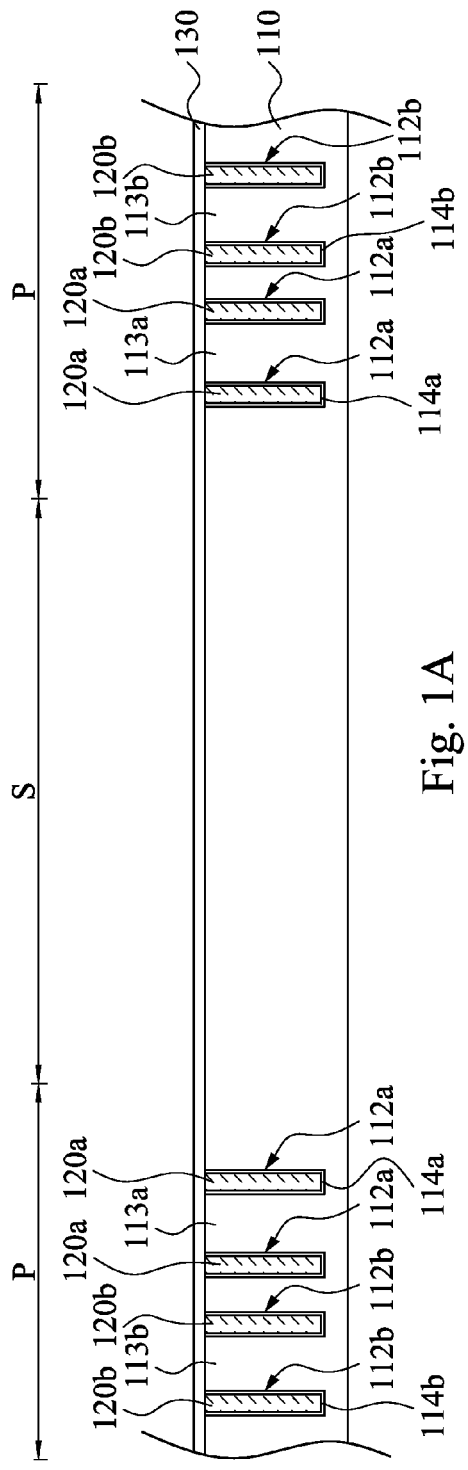

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

FIGS. 1A-1L are cross-sectional view of the method of forming an integrated circuit device in accordance with various embodiments of the present disclosure. The formation of a gas sensor 100 (see FIG. 1L) of the integrated circuit device is performed first. Reference is made to FIG. 1A. A substrate 110 is provided. In FIG. 1A, the substrate 110 can be a semiconductor material such as silicon. A sensing region S and a peripheral region P are defined in the substrate 110. The peripheral region P surrounds the sensing region S. In other words, the peripheral region P is outside the sensing region S.

Subsequently, a plurality of trenches 112a are formed in the substrate 110 to respectively define a plurality of first vias 113a, and a plurality of trenches 112b are formed in the substrate 110 to respectively define a plurality of second vias 113b. In some embodiments, the trenches 112a and 112b may be performed through an etching process. The trenches 112a and 112b do not extend all the way though the substrate 110. In other words, the trenches 112a and 112b are blind holes. In some embodiments, the edges of the trenches 112a and 112b can be oxidized through a thermal oxidation process. This coats the inner walls of the trenches 112a and 112b with dielectric oxide layers 114a and 114b, respectively. The numbers of the first vias 113a and the second vias 113b in FIG. 1A are illustrative, and should not limit the claimed scope of the present disclosure. In some embodiments, the numbers of the first vias 113a and the second vias 113b can be suitably selected according to actual situations.

Then, a plurality of isolation structures 120a and 120b are respectively formed in the trenches 112a and 112b. The isolation structures 120a respectively surround the first vias 113a, and the isolation structures 120b respectively surround the second vias 113b. The isolation structures 120a and 120b respectively provide isolation between the substrate 110 and the first vias 113a/the second vias 113b. In some embodiments, the isolation structures 120a and 120b are made of poly-silicon (poly-Si) or other suitable materials. The isolation structures 120a and 120b may be performed through a chemical-vapor deposition (CVD) process or other suitable methods.

In some embodiments, after the isolation structures 120a and 120b are respectively formed in the trenches 112a and 112b, a chemical-mechanical polishing (CMP) process can be performed to smooth out the top of the isolation structures 120a and 120b and prepare it for further processing.

A dielectric layer 130 is formed on the substrate 110 to cover the isolation plugs 120a and 120b. In some embodiments, the dielectric layer 130 can be made of an oxide material, and can be formed through a chemical-vapor deposition process. In some embodiments, the dielectric layer 130 are formed together with the thermal oxidation process of forming the dielectric oxide layers 114a and 114b. The dielectric layer 130 acts as an isolation layer between the substrate 110 and components formed on top of the dielectric layer 130. Also, the dielectric layer 130 is contributed to a good adhesion and stress balance of a membrane film 140 (see FIG. 1B) disposed thereon.

Figure 1B:
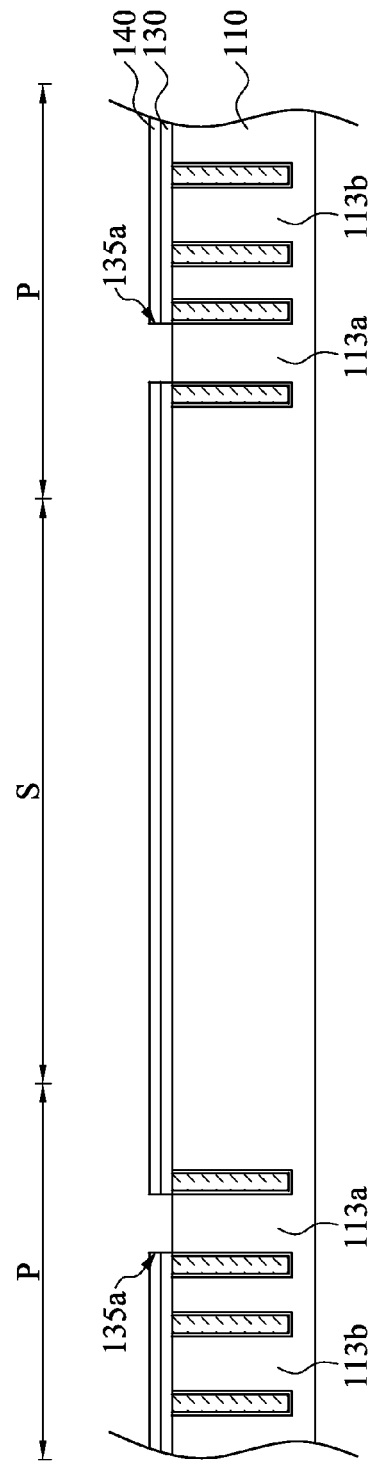

Reference is made to FIG. 1B. A membrane film 140 is formed on the dielectric layer 130. In FIG. 1B, the membrane film 140 substantially covers overall the dielectric layer 130, and the claimed scope is not limited in this respect. In some embodiments, the membrane film 140 can be made of silicon (Si), silicon dioxide ($SiO_2$), silicon nitride (SiN), silicon carbide (SiC), silicon oxynitride (SiON), or porous Si, and can be performed through a chemical-vapor deposition process.

Subsequently, the membrane film 140 and the dielectric layer 130 are patterned to form a plurality of through holes 135a both in the membrane film 140 and the dielectric layer 130. The through holes 135a are formed on the first vias 113a. Hence, the through holes 135a respectively expose the first vias 113a. In some embodiments, the through holes 135a may be patterned through an etching process.

Reference is made to FIG. 1C. A heater 150 is formed over the membrane film 140 and electrically connected to the first vias 113a through the through holes 135a. For example, a conductive layer (not shown) can be formed over the membrane film 140 and attached to the first vias 113a through the through holes 135a. The conductive layer is patterned to be the heater 150. In greater detail, the heater 150 includes a pattern portion 152 and at least two pads 154 electrically connected to the pattern portion 152. The pattern portion 152 is disposed on the sensing region S of the substrate 110, and the pads 154 are disposed on the peripheral region P of the substrate 110. The pads 154 are respectively and physically connected to the first vias 113a through the through holes 135a. The pattern of the pattern portion 152 can be arbitrary designed according to actual situations. In some embodiments, the conductive layer can be performed through a physical vapor deposition (PVD) process, and the conductive layer can be patterned through an etching process.

In some embodiments, the heater 150 has an electrical resistivity larger than about $6 \times 10^{-8}$ ohm-m. In some embodiments, the heater 150 has a melting point ranging from about 500 degrees Celsius to about 3000 degrees Celsius. The material satisfies the above conditions are, for example without limitation, tungsten (W) alloy, titanium tungsten (TiW), titanium aluminum nitride (TiAlN), tantalum aluminum (TaAl), chromiu (Cr), platinum (Pt), titanium nitride (TiN), molybdenum (Mo), poly-silicon (poly-Si), silicon carbide (SiC), tantalum nitride (TaN), tantalum oxide (TaO), or combination thereof.

Reference is made to FIG. 1D. A dielectric layer 160 is formed on and covers the heater 150. The dielectric layer 160 can be made of silicon nitride (SiN), and can be performed through a low pressure chemical vapor deposition (LPCVD) process. Subsequently, the dielectric layer 160, the membrane film 140, and the dielectric layer 130 are patterned to form a plurality of through holes 165b in the dielectric layer 160, the membrane film 140, and the dielectric layer 130. The through holes 165b are formed on the second vias 113b and separated from the through holes 135a. Hence, the through holes 165b respectively expose the second vias 113b. In some embodiments, the through holes 165b may be patterned through an etching process.

Figure 1E:
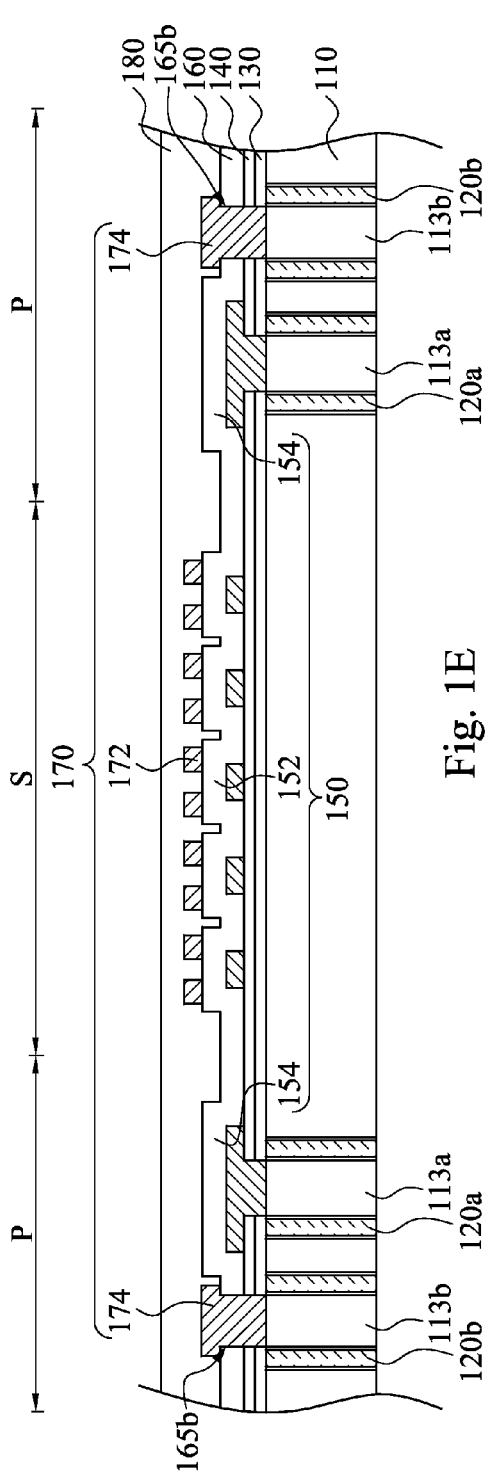

Reference is made to FIG. 1E. A sensing electrode 170 is formed on dielectric layer 160 and electrically connected to the second vias 113b through the through holes 165b. For example, another conductive layer (not shown) can be formed on the dielectric layer 160 and attached to the second vias 113b through the through holes 165b. Then, the conductive layer is patterned to be the sensing electrode 170. In greater detail, the sensing electrode 170 includes a pattern portion 172 and at least two pads 174 electrically connected to the pattern portion 172. The pattern portion 172 is disposed on the sensing region S of the substrate 110, and the pads 174 are disposed on the peripheral region P of the substrate 110. The pads 174 are respectively and physically connected to the second vias 113b through the through holes 165b. The pattern of the pattern portion 172 can be arbitrary designed according to actual situations. In some embodiments, the conductive layer can be performed through a physical vapor deposition (PVD) process, and the conductive layer can be patterned through an etching process. In some embodiments, the sensing electrode 170 can be made of tungsten (W) alloy, titanium tungsten (TiW), titanium aluminum nitride (TiAlN), tantalum aluminum (TaAl), titanium (Ti), titanium nitride (TiN), tantalum (Ta), tantalum nitride (TaN), tantalum oxide (TaO), tantalum silicon nitride (TaSiN), platinum (Pt), gold (Au), or combinations thereof.

Subsequently, a passivation layer 180 is formed and covers the sensing electrode 170. The passivation layer 180 can be made of silicon dioxide ($SiO_2$), and can be performed through a chemical vapor deposition (CVD) process. Then, a portion of the substrate 110 is removed from the bottom side thereof to expose the isolation structures 120a and 120b. For example, the portion of the substrate 110 is removed through a grinding process or other suitable processes.

Figure 1F:
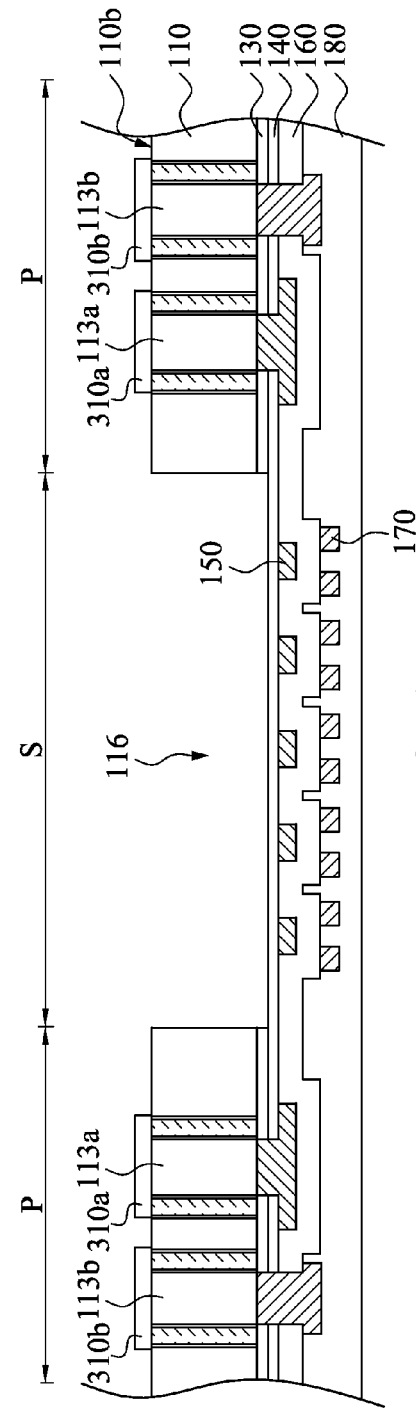

Reference is made to FIG. 1F. The structure in FIG. 1E is flipped over and disposed upside down. Then, a plurality of connecting elements 310a and 310b are formed on the bottom surface 110b of the substrate 110. The "bottom surface" herein is a surface opposite to the surface attaching to the dielectric layer 130. For example, another conductive layer is formed on the bottom side 110b of the substrate 110 and is patterned to be the connecting elements 310a and 310b. The connecting elements 310a and 310b are isolated and separated from each other. The connecting elements 310a are respectively connected to the first vias 113a, and the connecting elements 310b are respectively connected to the second vias 113b. The first vias 113a respectively interconnect the heater 150 and the connecting elements 310a, and the second vias 113b respectively interconnect the sensing electrode 170 and the connecting elements 310b. In some embodiments, the conductive layer can be performed through a physical vapor deposition (PVD) process, and the conductive layer can be patterned through an etching process. In some embodiments, the connecting elements 310a and 310b can be made of aluminum copper (AlCu) or other suitable materials.

Subsequently, an opening 116 is formed in the sensing region S of the substrate 110. The opening 116 exposes the membrane film 140. In some embodiments, the opening 116 is performed through an etching process. With this configuration, the membrane film 140 and layers disposed thereon can be suspended on the opening 116.

Reference is made to FIG. 1G. On the other hand, the formation of a complementary metal-oxide-semiconductor (CMOS) device 200 (see FIG. 1L) of the integrated circuit device is performed. It is noted that in some embodiments, the formation of the CMOS device 200 can be performed before the formation of the gas sensor 100 (see FIG. 1L). In some embodiments, the formation of the CMOS device 200 can be performed after the formation of the gas sensor 100. In some embodiments, the formations of the CMOS device 200 and the gas sensor 100 can be performed at the same time.

In FIG. 1G, a semiconductor structure 230 is formed on a second substrate 220. The semiconductor structure 230 may includes electric elements (not shown) and interconnect structures. The electric elements may include CMOS transistors, diodes, resistors, capacitors, inductors, and other active and passive semiconductor devices. The interconnect structures are configured to interconnect the electric elements. The interconnect structure includes a plurality of metallization layers including metal lines and vias (not shown) in a plurality of dielectric layers. The metal lines and vias may be formed of copper or copper alloys, and may be formed using the well-known damascene processes. The dielectric layers in the interconnect structure may be made of low-k dielectric material, extreme low-k dielectric material, or silicon. In other embodiments, the interconnect structure may include commonly known inter-layer dielectric (ILDs) and inter-metal dielectrics (IMDs). In FIG. 1G, the semiconductor structure 230 includes interconnect structures 232a and 232b.

Subsequently, a first substrate 210 is bonded to the semiconductor structure 230. Therefore, the semiconductor structure 230 is disposed between the first substrate 210 and the second substrate 220. In some embodiments, the first substrate 210 and the second substrate 220 can be made of silicon or other suitable materials.

Reference is made to FIG. 1H. In some embodiments, if the first substrate 210 is too thick, a thin down process can be performed to reduce the thickness of the first substrate 210. Then, a plurality of trenches 222a and 222b are formed in the first substrate 210 and a portion of the semiconductor structure 230. In some embodiments, the trenches 222a and 222b may be performed through an etching process. The trenches 222a and 222b respectively expose the interconnect structures 232a and 232b. In some embodiments, the edges of the trenches 222a and 222b can be oxidized through a thermal oxidation process. This coats the inner walls of the trenches 222a and 222b with dielectric oxide layers 224a and 224b, respectively, which provide isolation between the first substrate 210 and materials disposed in the trenches 222a and 222b.

Subsequently, a plurality of conductive plugs 240a and 240b are respectively formed in the trenches 222a and 222b. In some embodiments, the conductive plugs 240a and 240b are made of tungsten (W) or other suitable materials. The conductive plugs 240a and 240b may be performed through a chemical-vapor deposition (CVD) process or other suitable methods.

In some embodiments, after the conductive plugs 240a and 240b are respectively formed in the trenches 222a and 222b, a chemical-mechanical polishing (CMP) process can be performed to smooth out the top of the conductive plugs 240a and 240b and prepare it for further processing.

Figure 1I:
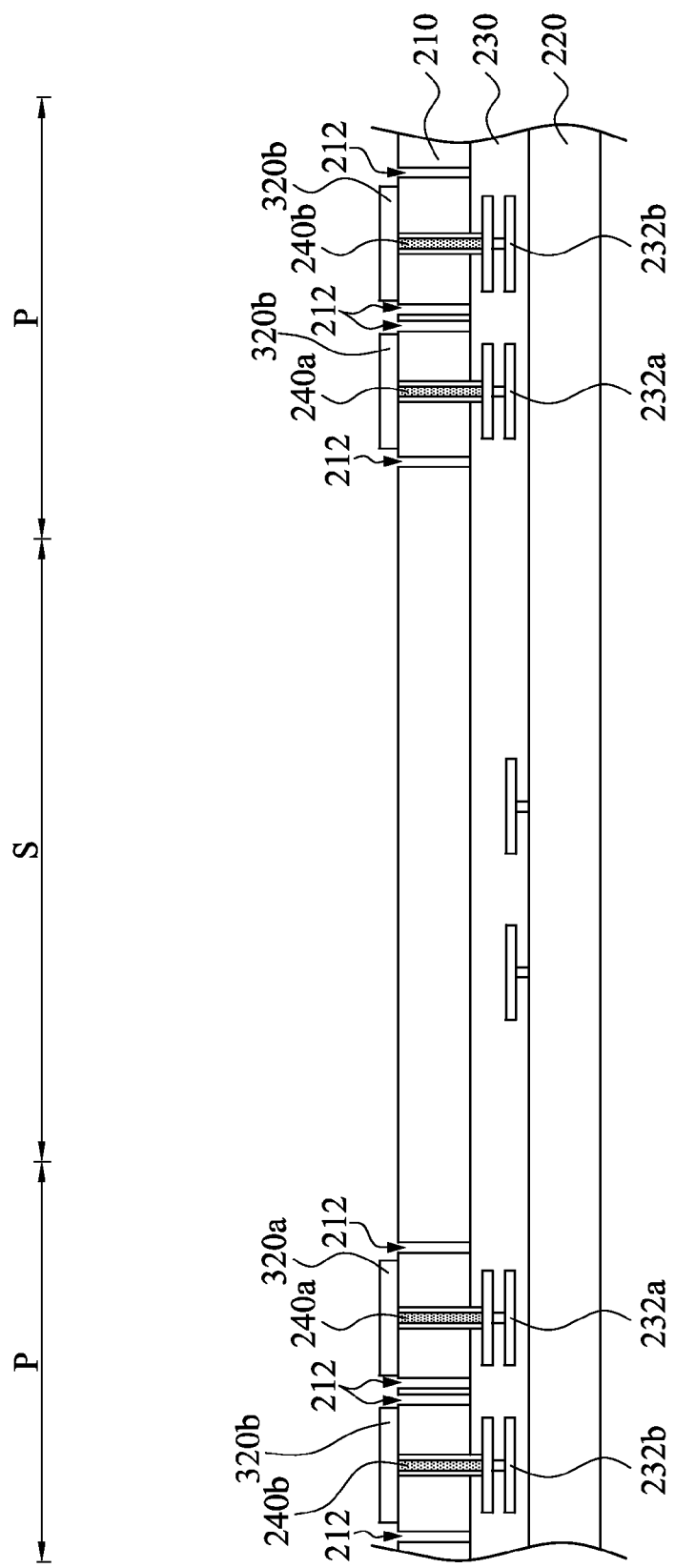

Reference is made to FIG. 1I. A plurality of connecting elements 320a and 320b are formed on the first substrate 210. For example, another conductive layer is formed on the first substrate 210 and is patterned to be the connecting elements 320a and 320b. The connecting elements 320a and 320b are isolated and separated from each other. The connecting elements 320a are respectively connected to the conductive plugs 240a, and the connecting elements 320b are respectively connected to the conductive plugs 240b. Hence, the connecting elements 320a can be respectively electrically connected to the interconnect structures 232a through the conductive plugs 240a, and the connecting elements 320b can be respectively electrically connected to the interconnect structures 232b through the conductive plugs 240b. In some embodiments, the conductive layer can be performed through a physical vapor deposition (PVD) process, and the conductive layer can be patterned through an etching process. In some embodiments, the connecting elements 320a and 320b can be made of germanium (Ge) or other suitable materials.

Subsequently, a plurality of trenches 212 are formed in the first substrate 210 to isolate the electrically signals between the conductive plugs 240a and 240b. In other words, the trenches 212 are respectively surrounds the conductive plugs 240a and 240b. In some embodiments, the trenches 212 may be performed through an etching process.

Figure 1J:
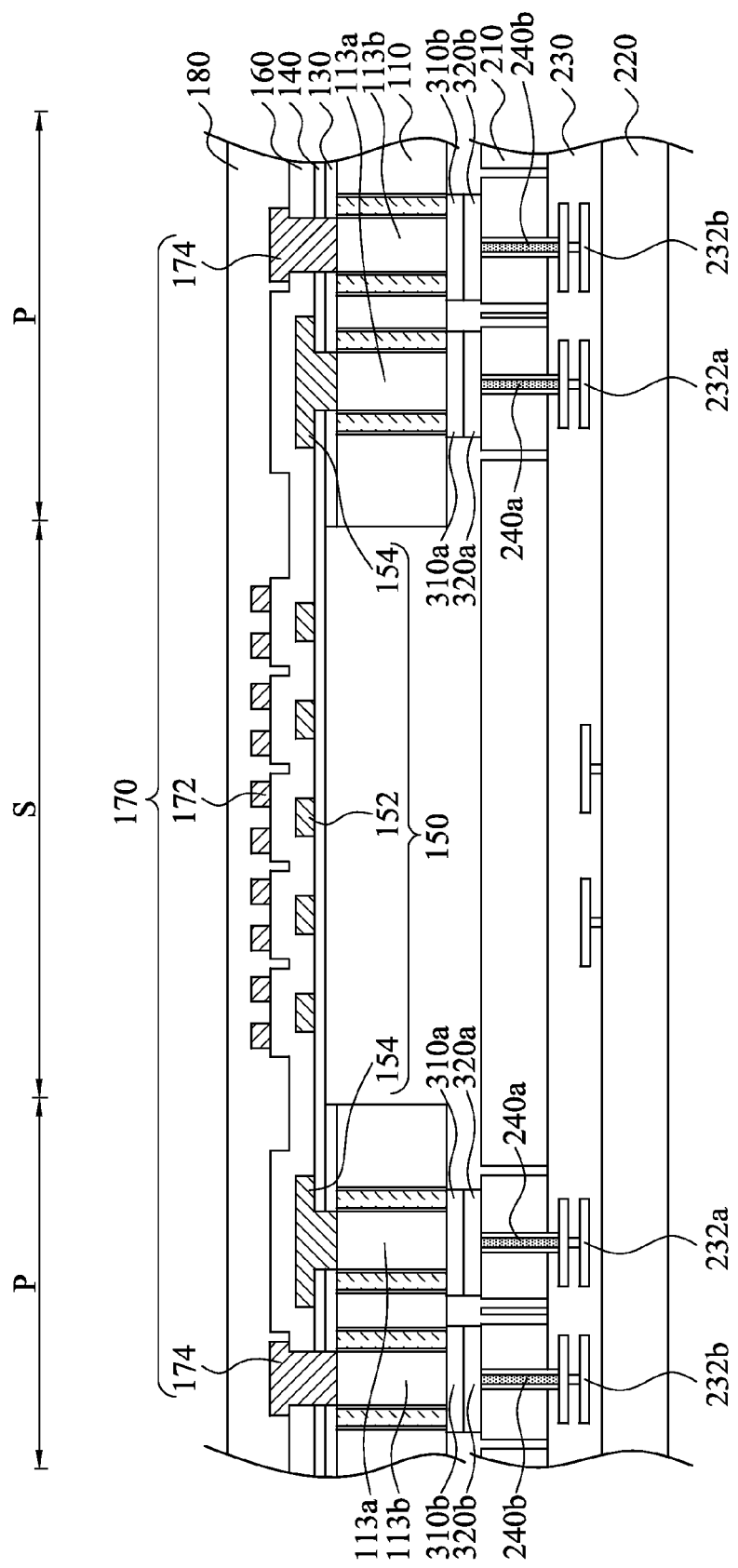

Reference is made to FIG. 1J. The structure of FIG. 1F is flipped over again and disposed on the structure of FIG. 1I. The connecting elements 320a and 320b are respectively bonded to the connecting elements 310a and 310b, for example, through a eutectic bonding process. A eutectic (wetting) reaction occurs between the connecting elements 310a and 310b and the connecting elements 320a and 320b, thereby forming eutectic alloy layer. The eutectic reaction is achieved by heating the connecting elements 310a, 310b, 320a, and 320b to their eutectic temperature, the temperature at which a combination of the connecting elements 310a, 310b, 320a, and 320b initially forms a liquid or molten state (eutectic state). When the connecting elements 310a, 310b, 320a, and 320b are at their eutectic temperatures, the materials at the interface of the connecting elements 310a, 310b, 320a, and 320b diffuse together to form an alloy composition, i.e., the eutectic alloy layer. Therefore, the structure of FIG. 1F and the structure of FIG. 1I can be bonded together.

In some embodiments, if the second substrate 220 is too thick, the structure of FIG. 1J can be flipped over again and a grinding process is performed to reduce the thickness of the second substrate 220.

Figure 1K:
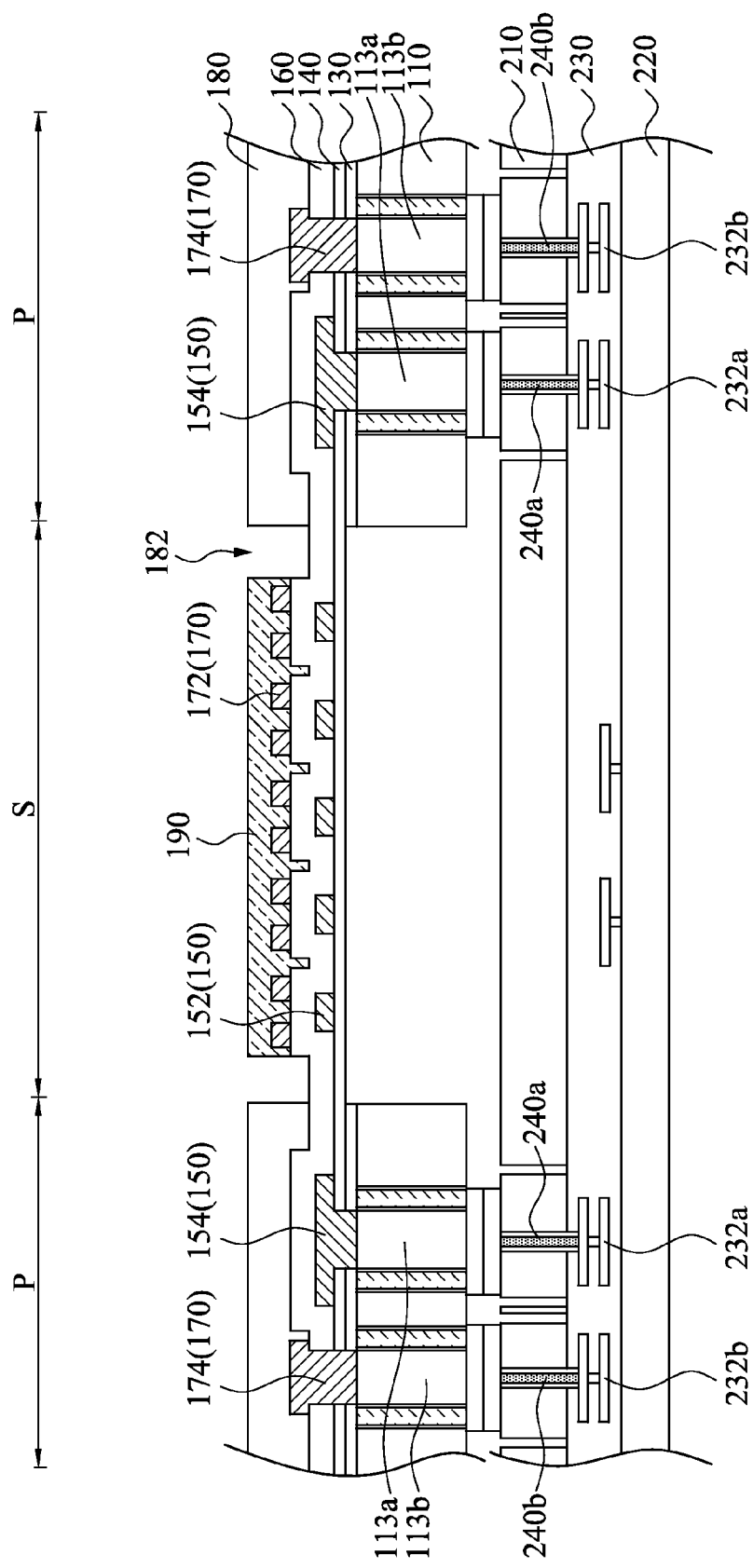

Reference is made to FIG. 1K. An opening 182 is formed in the passivation layer 180 and on the sensing region S of the substrate 110. The opening 182 exposes the pattern portion 172 of the sensing electrode 170 and a portion of the dielectric layer 160. In some embodiments, the opening 182 is performed through an etching process.

Subsequently, a gas sensitive film 190 is formed in the opening 182 and on the sensing electrode 170. In some embodiments, the gas sensitive film 190 may be formed using a method such as reactive sputtering, reactive vacuum evaporation, or other suitable methods. The gas sensitive film 190 can be made of metal oxide, such as tin oxide ($SnO_2$), zinc oxide (ZnO), indium oxide ($In_2O_3$), or other suitable materials, depending on the sensed gas.

Figure 1L:
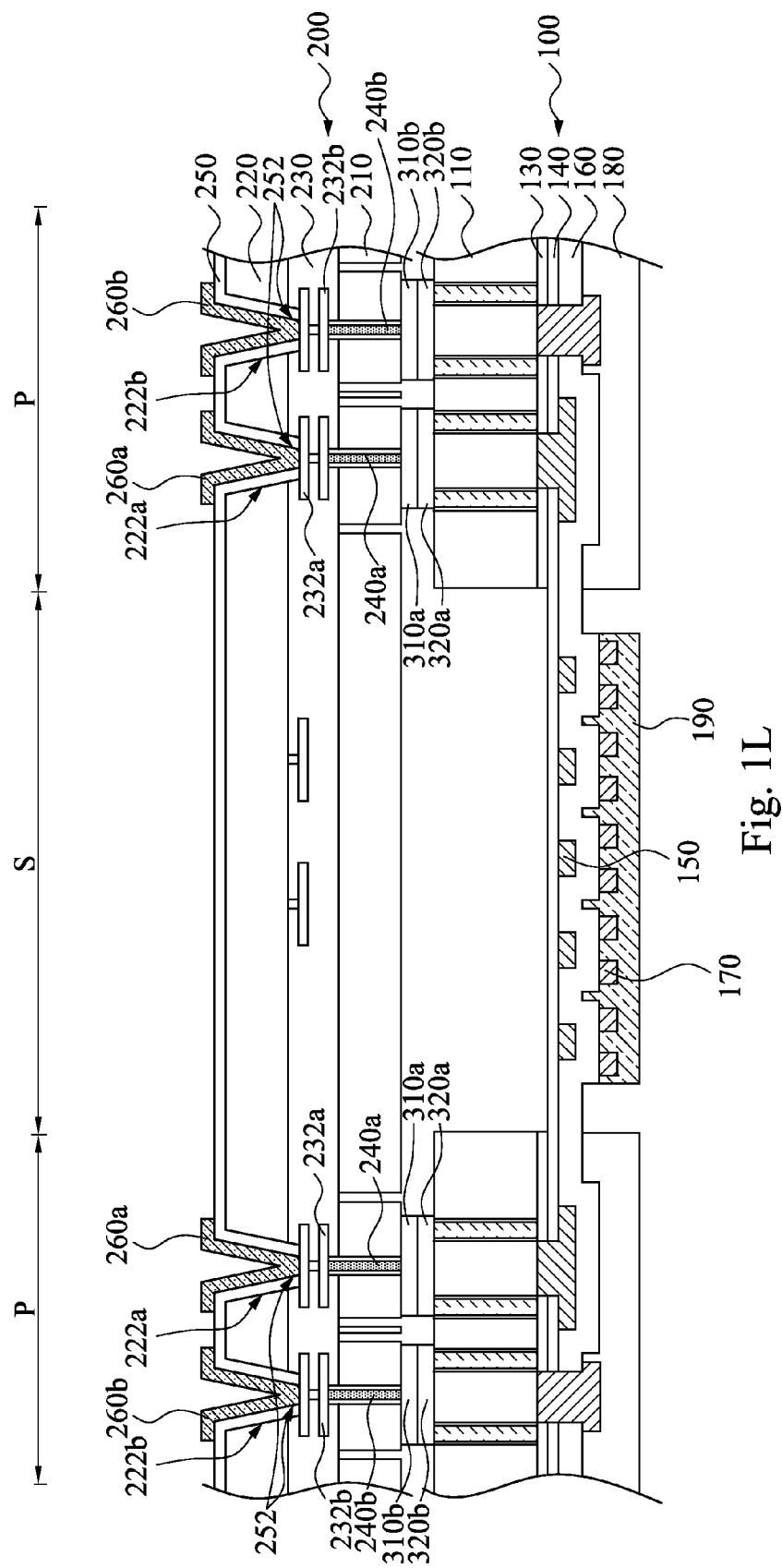

Reference is made to FIG. 1L. The structure in FIG. 1K is flipped over again. A plurality of through holes 222a and 222b are formed in the second substrate 220 and portions of the semiconductor structure 230 to respectively expose the interconnect structures 232a and 232b. In some embodiments, the through holes 222a and 222b are performed through an etching process. Then, a dielectric layer 250 is conformally formed on the second substrate 220. In some embodiments, the dielectric layer 250 can be made of an oxide material, and can be performed through a chemical-vapor deposition process. The dielectric layer 250 acts as an isolation layer between the second substrate 220 and components formed on top of the dielectric layer 250.

Subsequently, a plurality of openings 252 are formed in the dielectric layer 250 to respectively expose the interconnect structures 232a and 232b. Then, a plurality of contact 260a and 260b are respectively formed in the through holes 222a, 222b and the openings 252. For example, another conductive layer can be formed on the second substrate 220 and is patterned to form the contact 260a and 260b. The contacts 260a are electrically and physically connected to the interconnect structures 232a, and therefore are electrically connected to the heater 150. Moreover, the contacts 260b are electrically and physically connected to the interconnect structures 232b, and therefore are electrically connected to the sensing electrode 170. In some embodiments, the contact 260a and 260b may be made of aluminum copper (AlCu) or other suitable materials. In some embodiments, the contact 260a and 260b can be through silicon vias (TSVs), and the claimed scope is not limited in this respect.

Figure 2:
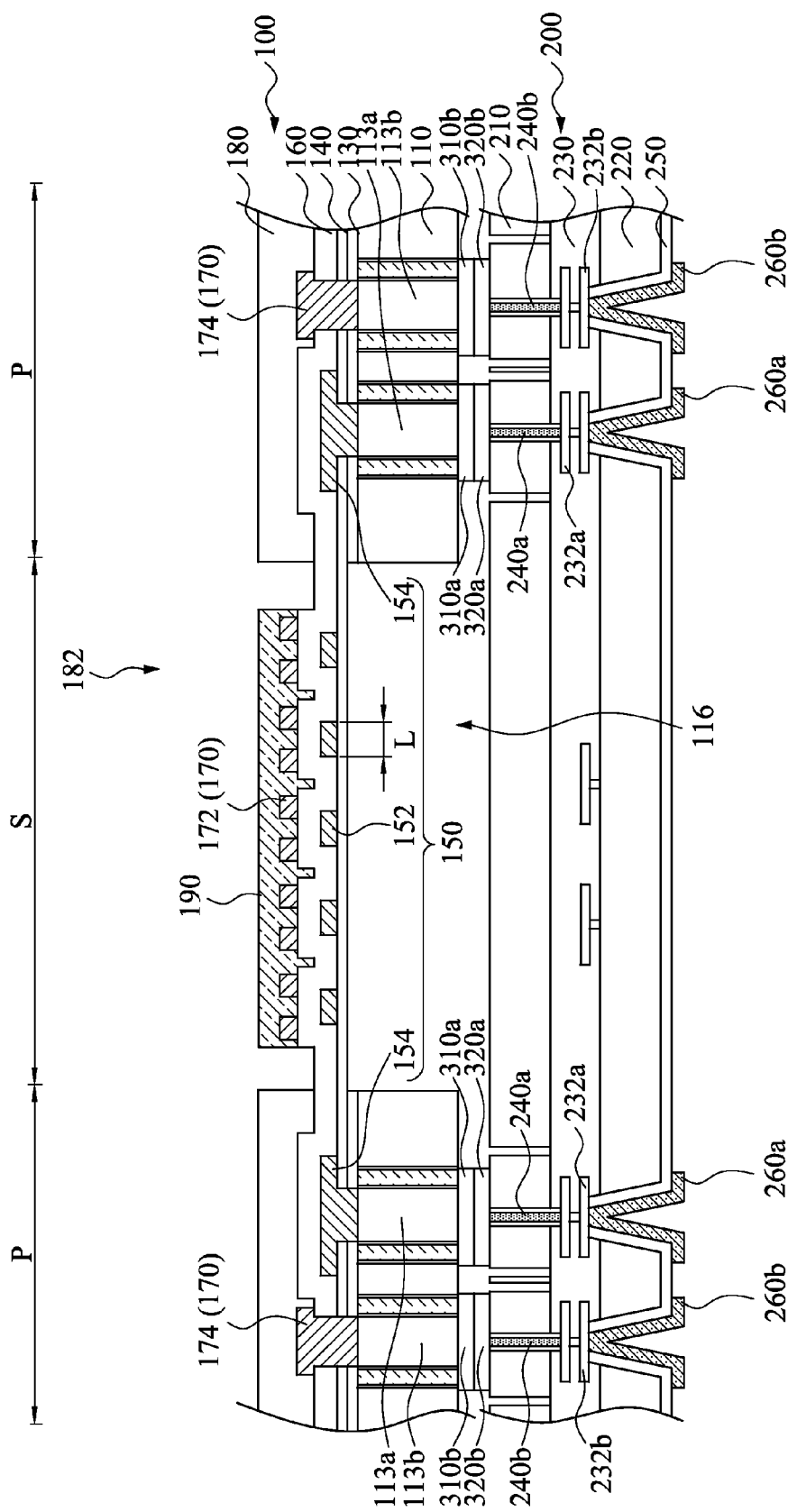
FIG. 2 is a cross-sectional view of the integrated circuit device of FIG. 1L after it is flipped over again.

FIG. 2 is a cross-sectional view of the integrated circuit device of FIG. 1L after it is flipped over again. The CMOS device 200 is disposed below the substrate 110 of the gas sensor 100. The connecting elements 310a, 310b, 320a, and 320b are disposed between and electrically connected to the gas sensor 100 and the CMOS device 200. Through the bonding of the gas sensor 100 and the CMOS device 200, the CMOS device 200 can control the gas sensor 100 and also receive the sensing information thereof. In greater detail, the CMOS device 200 provides a voltage to the heater 150, making the heater 150 generate heat. In some embodiments, the operation temperature of the gas sensor 100 is about 400 degrees Celsius to about 500 degrees Celsius or higher. The sensing electrode 170 is heated to the operation temperature. When a predetermined gas flows into the openings 116 and 182, the predetermined gas is sensed by the gas sensitive material 190, and the electrical resistivity of the sensing electrode 170 changes accordingly. Hence, the CMOS device 200 can measure the electrical resistivity of the sensing electrode 170 and sense the gas.

In some embodiments, the heater 150 has a melting point ranging from about 500 degrees Celsius to about 3000 degrees Celsius. Since the operation temperature of the heater is not too high, the melting temperature of the heater 150 may ranges from about 500 degrees Celsius to about 3000 degrees Celsius. The material satisfies the above conditions are, for example without limitation, tungsten (W) alloy, titanium tungsten (TiW), titanium aluminum nitride (TiAlN), tantalum aluminum (TaAl), chromiu (Cr), platinum (Pt), titanium nitride (TiN), molybdenum (Mo), poly-silicon (poly-Si), silicon carbide (SiC), tantalum nitride (TaN), tantalum oxide (TaO), or combination thereof. These materials can replace pure tungsten (W), which although has a higher melting point (about 3410 degrees Celsius) but causes stress problems in the gas sensor. The aforementioned materials improve stress problems caused by pure tungsten (W) during the manufacturing process.

In some embodiments, the electrical resistivity of the heater 150 is larger than about $6 \times 10^{-8}$ ohm-m, which is larger than the electrical resistivity of pure tungsten (W). Hence, the heating efficiency of the heater 150 is better than the pure tungsten (W). Furthermore, in some embodiments, a line width L of the pattern portion is about 0.1 μm to about 25 μm. With this small line width L, the resistance of the heater 150 can be further increased.

The gas sensor 100 and the CMOS device 200 are vertically stack to each other through the connecting elements 310a, 310b, 320a, and 320b. The word "vertical" herein is substantially a stack direction of layers (dielectric layer 130, membrane film 140, heater 150, dielectric layer 160, sensing electrode 170, the passivation layer 180, and the gas sensitive film 190) in the gas sensor 100. With this configuration, the layout area of the whole integrated circuit device can be reduced, and the size of the integrated circuit device can be reduced. The contact 260a, 260b and the conductive plugs 240a, 240b are disposed at opposite sides of the interconnect structures 232a, 232b. Therefore, the CMOS device 200 can communicate with external circuit from the backside (the side of CMOS device 200 opposite to the side bonding to the gas sensor 100) of the integrated circuit device. Furthermore, the substrate 110 can be a good heat isolation between the CMOS device 200 and the heater 150. Therefore, the substrate 110 can prevent the heat generated by the heater 150 from damaging the CMOS device 200.

Figure 3:
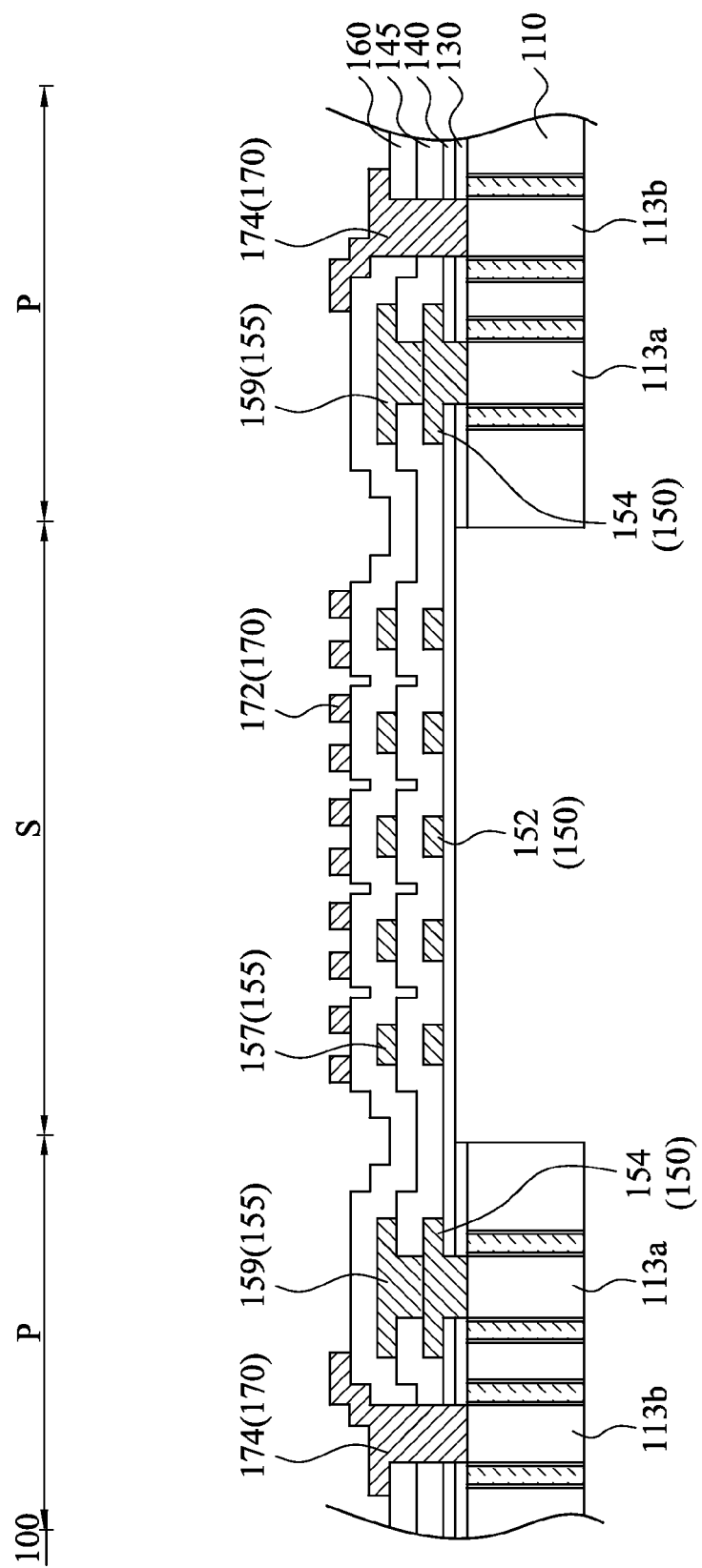
FIG. 3 is a gas sensor in accordance with various embodiments of the present disclosure.

In FIG. 2, the heater 150 includes a single layer. However, the claimed scope is not limited in this respect. FIG. 3 is a gas sensor 100 in accordance with various embodiments of the present disclosure. For clarity, the passivation layer 180 and the gas sensitive film 190 (see FIG. 2) are omitted in FIG. 3. In FIG. 3, the heater includes multiple layers, i.e., the heater layers 150 and 155. The heater layer 155 is disposed above the heater layer 150, and an additional dielectric layer 145 is disposed between the heater layers 150 and 155. The materials of the heater layers 150 and 155 can be the same or different. In FIG. 3, the pattern portions 152 and 157 of the heater layers 150 and 155 are the same. However, in some other embodiments, they can be different. In FIG. 3, the pads 154 and 159 of the heater layers 150 and 155 are connected to the same first vias 113a. However, in some other embodiments, they can be connected to different first vias 113a. In some other embodiments, the heater can include more than two layers stack to each other to increase the heating efficiency of the gas sensor 100. Other relevant structural details of FIG. 3 are similar to FIG. 2, and, therefore, a description in this regard will not be repeated hereinafter.

Figure 4:
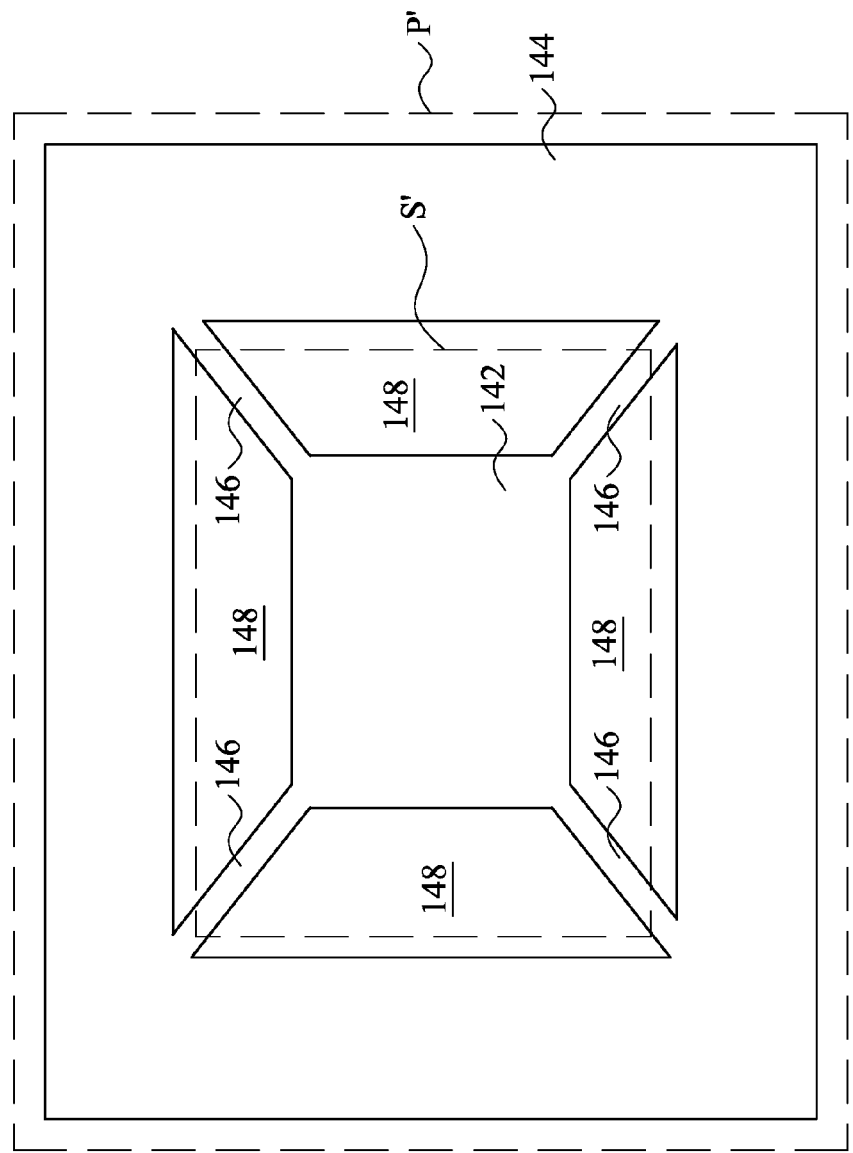
FIG. 4 is a top view of a membrane film in accordance with various embodiments of the present disclosure.

FIG. 4 is a top view of a membrane film 140 in accordance with various embodiments of the present disclosure. The area P' corresponds to the peripheral region P of the substrate 110 (see FIG. 2), and the area S' corresponds to the sensing region S (see FIG. 2) of the substrate 110. In FIG. 4, the membrane film 140 includes a suspended portion 142, a peripheral portion 144, and a plurality of bridge portions 146. The suspended portion 142 is disposed in the area S', i.e., disposed above the sensing region S of the substrate 110. The peripheral portion 144 surrounds the suspended portion 142, and is disposed in the area P', i.e., disposed above the sensing region P of the substrate 110. The bridge portions 146 respectively connect the suspended portion 142 and the peripheral portion 144. Therefore, two of the bridge portions 146, the suspended portion 142, and the peripheral portion 144 defines a through hole 148. Furthermore, the layers disposed above the membrane film 140 (i.e., the heater 150, the dielectric layer 160, the sensing electrode 170, the passivation layer 180, and the gas sensitive film 190 as shown in FIG. 2) all expose the through holes 148 of the membrane film 140. With this configuration, the heat generated from the heater 150 can be blocked in the area S' and is hard to leak to the peripheral portion 144. In some other embodiments, however, the through holes 148 of the membrane film 140 can be omitted, as shown in FIG. 2.

In the aforementioned embodiments, the heater has a melting point ranging from about degrees Celsius to about 3000 degrees Celsius. The materials satisfying this condition can replace pure tungsten (W), which although has a higher melting point (about 3410 degrees Celsius) but causes stress problems in the gas sensor. The aforementioned materials improve stress problems caused by pure tungsten (W) during the manufacturing process. Furthermore, the electrical resistivity of the heater is larger than about $6 \times 10^{-8}$ ohm-m. Hence, the heating efficiency of the heater is better than the pure tungsten (W).

According to some embodiments of the present disclosure, a gas sensor includes a substrate, a heater, a dielectric layer, a sensing electrode, and a gas sensitive film. The substrate has a sensing region and a peripheral region surrounding the sensing region, and the substrate further has an opening disposed in the sensing region. The heater is disposed at least above the opening, and the heater has an electrical resistivity larger than about $6\times10^{-8}$ ohm-m. The dielectric layer is disposed on the heater. The sensing electrode is disposed on the dielectric layer. The gas sensitive film is disposed on the sensing electrode.

According to some embodiments of the present disclosure, an integrated circuit device includes a gas sensor, a complementary metal-oxide-semiconductor (CMOS) device, and a plurality of connecting elements. The gas sensor includes a substrate, a heater, a dielectric layer, a sensing electrode, and a gas sensitive film. The substrate has a sensing region and a peripheral region outside the sensing region. The substrate further has an opening disposed in the sensing region. The heater is disposed at least above the opening. The heater has a melting point ranging from about 500 degrees Celsius to about 3000 degrees Celsius. The dielectric layer covers the heater. The sensing electrode is disposed on the dielectric layer. The gas sensitive film is disposed on the sensing electrode. The complementary metal-oxide-semiconductor device is disposed below the substrate of the gas sensor. The connecting elements are disposed between and electrically connected to the gas sensor and the complementary metal-oxide-semiconductor device.

According to some embodiments of the present disclosure, a method for manufacturing a gas sensor includes forming a heater at least on or above a sensing region of a substrate. The substrate has the sensing region and a peripheral region surrounding the sensing region. The heater has an electrical resistivity larger than about $6\times10^{-8}$ ohm-m. A dielectric layer is formed on the heater. A sensing electrode is formed on the dielectric layer. A gas sensitive film is formed on the sensing electrode.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A gas sensor comprising:
   a substrate having a sensing region and a peripheral region surrounding the sensing region, and the substrate further having an opening disposed in the sensing region;
   a heater disposed at least above the opening, wherein the heater has an electrical resistivity larger than about $6\times10^{-8}$ ohm-m;
   a membrane film disposed between the substrate and the heater, the membrane film having at least one through hole disposed at a border between the sensing region and the peripheral region of the substrate;
   a dielectric layer disposed on the heater;
   a sensing electrode disposed on the dielectric layer; and
   a gas sensitive film disposed on the sensing electrode.

2. The gas sensor of claim 1, wherein the heater is made of tungsten (W) alloy, titanium tungsten (TiW), titanium aluminum nitride (TiAlN), tantalum aluminum (TaAl), or combinations thereof.

3. The gas sensor of claim 1, wherein the heater comprises multiple layers.

4. The gas sensor of claim 1, wherein the heater comprises:
   a pattern portion disposed on the sensing region of the substrate; and
   a pad disposed on the peripheral region of the substrate and connected to the pattern portion.

5. The gas sensor of claim 4, wherein a line width of the pattern portion is about 0.1 µm to about 25 µm.

6. The gas sensor of claim 1, wherein the membrane film is made of silicon (Si), silicon dioxide ($SiO_2$), silicon nitride (SiN), silicon carbide (SiC), silicon oxynitride (SiON), or porous Si.

7. The gas sensor of claim 1, wherein the sensing electrode is made of tungsten (W) alloy, titanium tungsten (TiW), titanium aluminum nitride (TiAlN), tantalum aluminum (TaAl), titanium (Ti), titanium nitride (TiN), tantalum (Ta), tantalum nitride (TaN), tantalum oxide (TaO), tantalum silicon nitride (TaSiN), platinum (Pt), gold (Au), or combinations thereof.

8. A method for manufacturing a gas sensor, the method comprising:
   forming a heater at least above a sensing region of a substrate, wherein the substrate has a peripheral region surrounding the sensing region, and the heater has an electrical resistivity larger than about $6\times10^{-8}$ ohm-m;
   forming a membrane film between the substrate and the heater, the membrane film having at least one through hole disposed at a border between the sensing region and the peripheral region of the substrate;
   forming a dielectric layer on the heater;
   forming a sensing electrode on the dielectric layer; and
   forming a gas sensitive film on the sensing electrode.

9. The method of claim 8, wherein the heater is made of tungsten (W) alloy, titanium tungsten (TiW), titanium aluminum nitride (TiAlN), tantalum aluminum (TaAl), chromium (Cr), platinum (Pt), titanium nitride (TiN), molybdenum (Mo), poly-silicon (poly-Si), silicon carbide (SiC), tantalum nitride (TaN), tantalum oxide (TaO), or combinations thereof.

10. The method of claim 8, wherein a melting point of the heater is about 500 degrees Celsius to about 3000 degrees Celsius.

11. The method of claim 8, wherein the sensing electrode is made of tungsten (W) alloy, titanium tungsten (TiW), titanium aluminum nitride (TiAlN), tantalum aluminum (TaAl), titanium (Ti), titanium nitride (TiN), tantalum (Ta), tantalum nitride (TaN), tantalum oxide (TaO), tantalum silicon nitride (TaSiN), platinum (Pt), gold (Au), or combinations thereof.

12. The method of claim 8, further comprising:
   forming an isolation structure in the peripheral region of the substrate to define a via in the substrate, wherein the via is connected to the heater.

13. The method of claim 8, further comprising:
   forming an isolation structure in the peripheral region of the substrate to define a via in the substrate, wherein the via is connected to the sensing electrode.

14. A gas sensor comprising:
   a substrate comprising:
   an opening;
   at least one first via; and
   at least one second via isolated from the at least one first via, wherein the first via and the second via are present outside the opening;

a heater at least present on the opening of the substrate and connected to the first via of the substrate, wherein the heater has an electrical resistivity larger than about $6 \times 10^{-8}$ ohm-m;

a sensing electrode present on the heater and connected to the second via of the substrate;

a dielectric layer present between the heater and the sensing electrode; and a gas sensitive film connected to the sensing electrode.

15. The gas sensor of claim 14, further comprising:

at least one isolation structure present in the substrate and surrounding the first via.

16. The gas sensor of claim 14, further comprising at least one connecting element connected to the first via, wherein the first via is present between the heater and the connecting element.

17. The gas sensor of claim 14, further comprising at least one connecting element connected to the second via, wherein the second via is present between the sensing electrode and the connecting element.

* * * * *